United States Patent [19]

Hill et al.

[11] 4,125,711

[45] Nov. 14, 1978

[54] PROCESS FOR PREPARING AURANOFIN

[75] Inventors: David T. Hill, North Wales, Pa.; Ivan Lantos, Blackwood, N.J.; Blaine M. Sutton, Hatboro, Pa.

[73] Assignee: Smithkline Corporation, Philadelphia, Pa.

[21] Appl. No.: 811,665

[22] Filed: Jun. 30, 1977

[51] Int. Cl.$^2$ ............................................. C07H 23/00
[52] U.S. Cl. ................................... 536/121; 424/180; 536/4; 536/122
[58] Field of Search ..................................... 536/121, 4

[56] References Cited

U.S. PATENT DOCUMENTS 3,635,945  1/1972  Nemeth et al. ........................... 536/4

OTHER PUBLICATIONS

Coates et al., Aust. J. Chem. 19, 539–545 (1966).
Sutton et al., J. Med. Chem., 15, 1095 (1972).

*Primary Examiner*—Johnnie R. Brown
*Assistant Examiner*—Blondel Hazel
*Attorney, Agent, or Firm*—William H. Edgerton

[57] ABSTRACT

Auranofin is prepared by reacting 1-β-D-thio-2,3,4,6-tetra-O-acetylglucose with a triethylphosphine gold mercaptide.

5 Claims, No Drawings

PROCESS FOR PREPARING AURANOFIN

This invention comprises a new method for preparing the orally active gold containing antiarthritic agent, auranofin, which uses 1-β-D-thio-2,3,4,6-tetra-O-acetylglucose and a triethylphosphinegoldthio containing compound capable of reacting with the mercaptan group of the glucose compound.

Auranofin and its properties are reported in J. Med. Chem. 15, 1095 (1972) and U.S. Pat. No. 3,635,945. In these references auranofin is prepared by the reaction of an alkali metal salt of 1-thio-β-D-glucopyranose with a triethylphosphinegold halide.

The synthetic process of this invention is illustrated by the following:

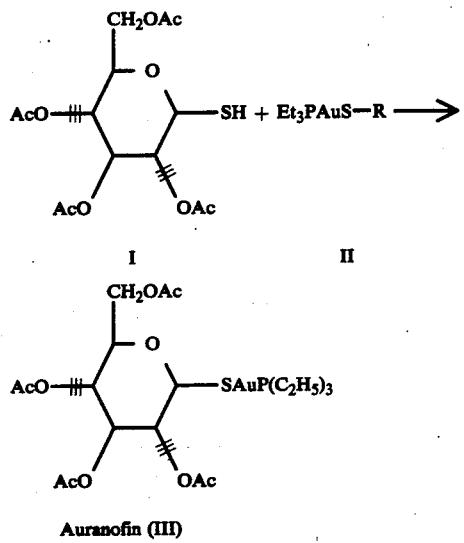

Auranofin (III)

In this reaction Ac is acetyl and R is alkyl such as, for convenience, substituted or unsubstituted, saturated or unsaturated alkyl groups having 1-8 carbons such as methyl, propyl, butyl, cyclohexyl, isobutyl, allyl or methylallyl, aralkyl such as benzyl or phenethyl, optionally substituted by trivial groups such as methyl, methoxy or halo, or triethylphosphinegoldthio [$(C_2H_5)_3$PAuS—].

The starting materials for the method of this invention are either known or are prepared by methods known to the art. For example the thioglucopyranose (I) is an old compound, see Whistler, Methods in Carbohydrate Chemistry, Academic Press, Vol. 2, 436 (1963). The triethylphosphinegold mercaptides (II) are prepared by reacting triethylphosphinegold bromide or chloride with a known thiol in the presence of one mole equivalent of base usually in ethanol-chloroform solution, see Aust. J. Chem. 19, 539 (1966).

The reaction of this invention is carried out by reacting the thiol and mercaptide starting materials in approximately equimolar quantities in an organic solvent in which the reactants are soluble and which is inert toward the reactants, such as a common halogenated hydrocarbon for example chloroform, carbon tetrachloride, methylene chloride or ethylene tetrachloride, a benzenoid solvent such as benzene, toluene or xylene, dimethylformamide, dimethylacetamide, diethylcarbonate, common ethereal solvents such as ethyl ether or dioxane, ethyl acetate, dimethyl sulfoxide or lower alkanols such as methanol, ethanol or isopropanol.

Usually the reaction is run at room temperature for from 1 hour to 48 hours depending on the reactivity of the starting material or the size of the run. The reaction however may be optionally run over a wide range of temperatures such as from room temperature up to the boiling point of the reaction mixture, most conveniently from 25°–75°. The reaction product is isolated by standard chemical methods such as evaporation of the solvent and purification of the residue by chromatography or fractional crystallization.

The following examples are designed for illustration of the reaction of this invention. All temperatures are Centigrade.

EXAMPLE 1

A chloroform solution (30 ml) of 1.0 g (2.8 mmoles) of methylthio(triethylphosphine)gold and 1.0 g (2.8 mmoles) of 1-β-thio-2,3,4,6-tetra-O-acetylglucose was stirred at room temperature for 3 hours. After filtration, the solvent was removed at reduced pressure and the resultant oil treated with methanol (1.5 ml). The tacky solid which formed was removed and recrystallized from methanol-water (3:5) at −23° to give 1.0 g (55%) of S-triethylphosphinegold 2,3,4,6-tetra-O-acetyl-1-thio-β-D-glucopyranoside (auranofin), m.p. 108°–110°; $[\alpha]_D^{25}$ (1% methanol) = −53.9°.

Other mercaptides may be substituted in equimolar quantities in this reaction such as ethylthio(triethylphosphine)gold, i-butylthio(triethylphosphine)gold, allylthio(triethylphosphine)gold, propylthio(triethylphosphine)gold or benzylthio(triethylphosphine)gold.

EXAMPLE 2

A chloroform solution (200 ml) of 5.6 g (15.9 mmoles) of chloro(triethylphosphine)gold (I) was stirred together with 3.8 g (15.9 mmoles) of sodium sulfide monohydrate in water (80 ml) at room temperature for 2 hours. The chloroform layer was separated and washed with water (1 × 100 ml), dried (magnesium sulfate) and the solvent removed at reduced pressure to give 6.3 g of yellow solid. This material was dissolved in benzene and ether added dropwise to induce crystal formation. The mixture was cooled and additional ether added until formation of product ceased. The cream colored material decomposed at 220°, bis[(triethylphosphine)-aurous]sulfide.

A chloroform solution (25 ml) of 1.8 g (1.5 mmoles) of bis[(triethylphosphine)aurous]sulfide and 0.55 g of 2,3,4,6-tetra-O-acetyl-1-thio-β-D-glucopyranose was stirred overnight at room temperature. The solvent was removed at reduced pressure and the residue chromatographed (silica gel/chloroform) to give 0.9 g of colorless oil. Two crystallizations from methanol-water gave auranofin, m.p. 112°–116°, $[\alpha]_D^{25}$ (1% methanol) = −56.3°.

What is claimed is:

1. The method of preparing auranofin comprising reacting 1-β-D-thio-2,3,4,6-tetra-O-acetylglucose with a mercaptide of the formula:

$(C_2H_5)_3$PAuS—R in which R is lower alkyl of 1–8 carbons, benzyl or triethylphosphinegoldthio; in an organic solvent in which the reactants are soluble and which is inert toward the reactants.

2. The method of claim 1 in which R is methyl.

3. The method of claim 2 in which the solvent is methylene chloride.

4. The method of claim 1 in which R is triethylphosphinegoldthio.

5. The method of claim 4 in which the solvent is methylene chloride.